United States Patent [19]

Masuko et al.

[11] 4,350,829
[45] Sep. 21, 1982

[54] PROCESS FOR PREPARING ISOBUTYRIC ACID

[75] Inventors: Tatsuo Masuko; Shigeo Fukaya; Nobuyuki Murai, all of Yokkaichi; Jun Noma, Isshi, all of Japan

[73] Assignee: Mitsubishi Chemical Industries, Limited, Tokyo, Japan

[21] Appl. No.: 52,590

[22] Filed: Jun. 27, 1979

[30] Foreign Application Priority Data

Jul. 14, 1978 [JP] Japan ................................ 53-85834
Jul. 14, 1978 [JP] Japan ................................ 53-85835
Jul. 14, 1978 [JP] Japan ................................ 53-85836
Jul. 21, 1978 [JP] Japan ................................ 53-89125
Jul. 21, 1978 [JP] Japan ................................ 53-89126

[51] Int. Cl.$^3$ ................ C07C 51/235; C07C 51/295; C07C 53/124

[52] U.S. Cl. ................................ 562/531; 568/389; 568/577; 568/881

[58] Field of Search ................ 562/606, 531; 260/413

[56] References Cited

U.S. PATENT DOCUMENTS 2,010,358 8/1935 Groll et al. ........................... 562/531
2,930,801 3/1960 Montagna et al. .................. 562/531

Primary Examiner—Vivian Garner
Attorney, Agent, or Firm—Oblon, Fisher, Spivak, McClelland & Maier

[57] ABSTRACT

There is disclosed a process for the production of isobutyric acid by liquid-phase oxidation of isobutyraldehyde in the presence of an alkali metal-containing compound, the oxidation being effected while maintaining the molar ratio of oxygen to isobutyraldehyde to be fed at 0.5 or above.

2 Claims, No Drawings

PROCESS FOR PREPARING ISOBUTYRIC ACID

BACKGROUND OF THE INVENTION

1. Field of the Invention

This invention relates to a process for preparing isobutyric acid.

More specifically, this invention relates to a process for preparing isobutyric acid by oxidation of isobutyraldehyde with a molecular oxygen-containing gas.

2. Description of the Prior Art

Isobutyric acid is useful as a food additive or as a starting material for the production of methacrylic acid and methyl methacrylate.

It is known to oxidize isobutyraldehyde with molecular oxygen in the presence of a catalyst in order to prepare isobutyric acid as described in, for example, J. Org. Chem., 26, 565 (1961); British Pat. No. 824,116 and Japanese Patent Publication No. 39010/77. However, these prior art processes are not satisfactory in terms of selectivity to isobutyric acid, conversion of isobutyraldehyde and selectivity to by-products such as acetone (hereinafter referred to as "AT"), peroxides (hereinafter referred to as "PO"), isopropyl alcohol (hereinafter referred to as "IPA") and the like.

It has now been found that the above-mentioned problems can be solved by a new improved process and this invention has been accomplished.

SUMMARY OF THE INVENTION

There is provided a process for preparing isobutyric acid by continuous liquid-phase oxidation of isobutyraldehyde with molecular oxygen or a molecular oxygen-containing gas in the presence of an alkali metal-containing compound, the improvement comprising maintaining the molar ratio of oxygen to isobutyraldehyde to be fed at 0.5 or above.

DETAILED DESCRIPTION OF THE PREFERRED EMBODIMENTS

This invention is directed to the process for preparing isobutyric acid by continuous liquid-phase oxidation of isobutyraldehyde with molecular oxygen or a molecular oxygen-containing gas in the presence of an alkali metal-containing compound, the improvement comprising maintaining the molar ratio of oxygen to isobutyraldehyde to be fed at 0.5 or above.

Further details of the present invention will be given in the following description.

The alkali metal compounds which are used in the reaction system include alkali metal salts such as potassium or sodium salts, preferably alkali metal salts of isobutyric acid, for example, potassium isobutyrate and sodium isobutyrate. The alkali metal compound should be present in an amount of 0.01 to 1 mole, preferably 0.05 to 0.5 mole, per liter of the reaction solution. Alternatively, an alkali metal carbonate or hydroxide may be added to the reaction system as the alkali metal compound. The molecular oxygen-containing gas used for the oxidation of isobutyraldehyde may usually be air or a mixture of oxygen and an inert diluent gas such as nitrogen containing at least 5% by volume of oxygen.

Stirred tank reactor or bubbling column is used as a oxidation reactor.

The average residence time in the oxidation reactor is 1 to 10 hours, preferably 2 to 8 hours.

The oxidation according to this invention is conducted generally at a temperature of 50° to 70° C., preferably 55° to 65° C. and at a pressure of from atmospheric to 10 kg/cm$^2$ (gage), preferably from 3 to 8 kg/cm$^2$ (gage).

In the liquid-phase oxidation such as the oxidation of isobutyraldehyde, where the conversion is low, the reaction rate increases as the absorption rate of oxygen becomes more rate-determining.

On the other hand, where the conversion is high, the reaction rate lowers extremely. Accordingly, in order for the conversion to be close to 100%, it is necessary to use the severe reaction conditions, e.g., high reaction temperature and long residence time.

In order for the process of this invention to be economically attractive, two reactors are used, the former being used for the fast portion of the reaction of the latter being used for the slow portion of the reaction.

In the fast portion of the reaction, the percent conversion of isobutyraldehyde is usually 90–95%.

In order to avoid explosion in the gas phase, it is necessary to feed as little oxygen as possible and to maintain the oxygen concentration of the off-gas at as low level as possible.

It will follow from the above that the preferred molar ratio of O$_2$ to isobutyraldehyde to be fed is less than 0.5.

However, the use of the molar ratio of O$_2$ to isobutyraldehyde of less than 0.5 is economically disadvantageous in that the amount of by-products increases and that both the conversion of isobutyraldehyde and the selectivity to isobutyric acid decrease.

Therefore, it is an essential feature of this invention to feed oxygen at a molar ratio of oxygen to isobutyraldehyde of at least 0.5, preferably at least 0.54.

However, an excessive increase in the molar ratio of O$_2$ to isobutyraldehyde results in the danger of explosion. In addition, in view of the restriction resulting from the cost for oxygen, it is preferred to control the oxygen concentration of the reactor off-gas outside the range of explosion.

The oxygen concentration of the reactor off-gas is between 1 percent by volume and the lower explosion limit, preferably between 3 percent and 8 percent by volume. When the oxygen concentration of the reactor off-gas is less than 1%, the amount of by-products such as acetone, peroxides, isopropyl alcohol and the like increase, and the selectivity of isobutyraldehyde to isobutyric acid as well as the yield of isobutyric acid decreases.

In view of the danger of explosion, the oxygen concentration of the off-gas should fall outside the range of explosion, that is, lower than the lower explosion limit.

The value for the lower explosion limit of the oxygen concentration of the reactor off-gas varies with the temperature, pressure and the like.

The reaction system is preferably controlled so as to maintain the water content of the reaction solution at 2.5% by weight or below, more preferably 2.0% or below. In the process according to this invention, isobutyraldehyde is continuously oxidized with molecular oxygen. For this purpose, either a continuous process in which both the isobutyraldehyde and oxygen are fed continuously or a semi-batch process in which only the oxygen is fed continuously may be employed.

In a preferred embodiment of this invention, the oxidation is conducted in its first-stage in a bubbling column at a temperature of 50° to 70° C. with the percent conversion being kept at 95% or below and subsequently the effluent of the bubbling column is subjected to further oxidation in at least one stirred tank reactor at a temperature equal to or higher than the temperature employed in the first-stage oxidation.

The first-stage oxidation in a bubbling column is conducted under the conditions described above.

It is economically disadvantageous to effect the oxidation in a bubbling column-type reactor at higher than 95% conversion. For this reason, following the first stage of the oxidation in the bubbling column which is effected at not higher than 95% conversion, preferably 90 to 95% conversion, one or more stirred tank reactors are used to proceed with the oxidation.

If the second stage of the oxidation is effected in a bubbling column-type reactor in which mixing is achieved by bubbles, a much larger amount of oxygen is required for oxidation and this is not economically favorable. The second stage of the oxidation is effected preferably at a temperature of at least 5° C. above the temperature in the first-stage oxidation, more preferably at a temperature of 70° to 85° C.

The average residence time in the second-stage reactor or reactors is generally 2 to 3 hours.

At the end of the second-stage oxidation, the reaction mixture is heated at 100° to 200° C. for 3 to 20 minutes under pressure in order to decompose any peroxide by-product and is then passed to a flash evaporator operated at a pressure of atmospheric to 2 kg/cm$^2$ (gage) and a temperature of 160° to 200° C. to evaporate the desired product, isobutyric acid and unreacted isobutyraldehyde and other materials. A portion (approximately 10%) of the residual high boiling materials and catalyst (e.g., potassium isobutyrate) is removed out of the reaction system and discarded, while the remaining portion is recycled for reuse in the reactor.

In accordance with this embodiment, isobutyric acid can be produced with high percent conversion, in high yields and with shorter residence time in the reactors.

Therefore, this embodiment is of great advantage in the commercial production of isobutyric acid.

Many modifications can be made to the process of this invention.

It is one aspect of the process of this invention to recycle into the reactor a portion of the reaction solution withdrawn from the reactor. In this regard, a sufficient amount of the reaction solution should be recycled so that the recycled reaction solution has an internal linear velocity of at least 5 m/hr., preferably at least 10 m/hr.

The reaction solution can be recycled into the reactor, for example, by any of the following procedures:

I. The overflow from the top portion of the reactor is put back to the reactor at the bottom.

II. The reaction solution is withdrawn from the bottom portion of the reactor and returned to the reactor in the upper portion.

III. The reaction solution is withdrawn from the upper portion of the reactor and returned to the reactor in the bottom portion.

Among these procedures, Procedure I is preferred since Procedure II involves some problems with respect to the short path of the starting material, gas separation and control of the liquid level and Procedure III also involves some problems in terms of control of the liquid level.

In accordance with this embodiment, isobutyric acid can be produced with high percent conversion and high rate of reaction.

In a more preferred embodiment of this invention, a portion of the reaction solution is withdrawn from the first stage bubbling column-type reactor and recycled to the first stage reactor.

In the process of this invention, the amount of the by-products can be controlled at low level, and isobutyric acid can be produced with high percent conversion, in high yields and with high rate of reaction.

Having generally described this invention, a more complete understanding can be obtained by reference to comparative examples and examples which are provided herein for purposes of illustration only and are not intended to be limiting in any manner.

EXAMPLE 1

A 300 ml jacketed reaction vessel equipped with a stirrer was charged with 250 ml of isobutyric acid (hereinafter referred to as "IBAC") containing 0.1 mol/l of potassium, and was heated to 60° C. Subsequently, a solution having the composition described below and air were fed at rates of 100 cc/hr. and 56.2 Nl/hr., respectively (molar ratio of $O_2$ to isobutyraldehyde (hereinafter referred to as "IBD"):0.54), and the reactor was operated at a pressure of 5 kg/cm$^2$ (gage) with an average residence time of 3 hours.

| | (% by weight) |
|---|---|
| I B D | 85.7 |
| I B A C | 12.48 |
| Potassium isobutyrate (hereinafter referred to as "IBAK") | 1.50 |
| H$_2$O | 0.32 |

The oxygen concentration of the reactor off-gas was 4.2% by volume.

The reaction mixture which was withdrawn from the reactor was passed through a condenser. Thereafter, gas and liquid were separated. The reaction solution and the gas were subjected to gas-chromatographic analysis to determine their composition.

The data obtained in this example in terms of selectivities to AT, PO, IPA and IBAC, and conversion of IBD are shown in Table 1 below.

EXAMPLE 2

Example 1 was repeated except that air was fed at a rate of 69.9 Nl/hr. (molar ratio of $O_2$ to IBD:0.67).

The results are shown in Table 1 below.

EXAMPLE 3

Example 1 was repeated except that the water content of the solution was 3.66% by weight and air was fed at a rate of 61.7 Nl/hr. (molar ratio of $O_2$ to IBD:0.62)

The results are shown in Table 1 below.

EXAMPLE 4

Example 1 was repeated except that the solution and air were fed at rates of 186 cc/hr. and 203.2 Nl/hr. (molar ratio of $O_2$ to IBD:1.07), respectively, and an average residence time was 1.6 hours.

EXAMPLE 5

Example 1 was repeated except that air was fed at a rate of 55.6 Nl/hr. (molar ratio of $O_2$ to IBD:0.50).

The results are shown in Table 1 below.

COMPARATIVE EXAMPLE 1

Example 1 was repeated except that air was fed at a rate of 54.9 Nl/hr. (molar ratio of $O_2$ to IBD:0.47). The results are shown in Table 1 below.

EXAMPLE 6

A 300 ml jacketed reaction vessel equipped with a stirrer was charged with 250 ml of IBAC containing 0.1 mol/l of potassium, and was heated to 60° C. Subsequently, a solution having the composition described below and air were fed at rates of 58.5 cc/hr. and 33.9 Nl/hr., respectively (molar ratio of $O_2$ to IBD:0.57), and the reactor was operated at a pressure of 5 kg/cm² (gage) with an average residence time of 5 hours.

|  | (% by weight) |
|---|---|
| IBD | 85.5 |
| IBAC | 12.5 |
| IBAK | 1.61 |
| $H_2O$ | 0.38 |

Then, the same procedure as described in Example 1 was used.
The results are shown in Table 1 below.

EXAMPLE 7

Example 6 was repeated except that air was fed at a rate of 41.8 Nl/hr. (molar ratio of $O_2$ to IBD:0.70).
The results are shown in Table 1 below.

COMPARATIVE EXAMPLE 2

Example 6 was repeated except that air was fed at a rate of 17.2 Nl/hr. (molar ratio of $O_2$ to IBD:0.29)
The results are shown in Table 1 below.

TABLE 1

| | $\frac{O_2 \text{ fed}}{\text{IBD fed}}$ (molar ratio) | Average residence time (hr.) | Oxygen concentration of the reactor off-gas (% by volume) | % Selectivity* to by-products (molar basis) AT | PO | IPA | % Selectivity* to IBAC (molar basis) | % Conversion of IBD (molar basis) |
|---|---|---|---|---|---|---|---|---|
| Example 1 | 0.54 | 3.0 | 4.2 | 1.80 | 1.51 | 0.79 | 92.5 | 92.7 |
| Example 2 | 0.67 | 3.0 | 7.5 | 1.54 | 0.97 | 0.28 | 94.2 | 92.4 |
| Example 3 | 0.62 | 3.0 | 5.5 | 2.3 | 1.15 | 0.74 | 92.0 | 95.8 |
| Example 4 | 1.07 | 1.6 | 13.6 | 1.33 | 1.08 | 0.25 | 94.6 | 84.1 |
| Example 5 | 0.50 | 3.0 | 3.5 | 1.88 | 2.38 | 1.34 | 88.8 | 91.0 |
| Comparative Example 1 | 0.47 | 3.0 | 2.6 | 3.73 | 6.22 | 2.64 | 82.6 | 73.0 |
| Example 6 | 0.57 | 5 | 2.2 | 2.18 | 1.67 | 0.44 | 93.4 | 96.6 |
| Example 7 | 0.70 | 5 | 7.5 | 2.05 | 1.65 | 0.51 | 92.6 | 95.8 |
| Comparative Example 2 | 0.29 | 5 | 0.82 | 2.71 | 7.19 | 2.66 | 81.4 | 75.5 |

*Based on the reacted IBD

When the results of Examples 1 to 7 are compared with those of Comparative Examples 1 and 2, it is clear that when the molar ratio of $O_2$ to IBD to be fed is less than 0.50, both the selectivity to IBAC and the conversion of IBD are low.

EXAMPLE 8

Example 1 was repeated except that air was fed at a rate of 59.1 Nl/hr. (molar ratio of $O_2$ to IBD:0.58).
The water content of the reaction solution outlet was 0.54% by weight.
The oxygen content of the reactor off-gas was 5.4% by volume.
The data obtained in this example in terms of selectivity to AT, PO, IPA and IBAC are shown in Table 2 below.

EXAMPLE 9

Example 8 was repeated except that water was fed at a rate of 0.082 mol/hr.
The water content of the reaction solution outlet was 2.02% by weight.
The results are shown in Table 2 below.

EXAMPLE 10

Example 8 was repeated except that water and air were fed at rates of 0.165 mol/hr. and 61.7 Nl/hr. (molar ratio of $O_2$ to IBD:0.62), respectively. The water content of the reaction solution outlet was 3.66% by weight.
The results are shown in Table 2 below.

TABLE 2

| | $\frac{O_2 \text{ fed}}{\text{IBD fed}}$ (molar basis) | Oxygen concentration of the reactor off-gas (% by volume) | Water content of the reaction solution outlet (% by weight) | % Selectivity* to by-products (molar basis) AT | PO | IPA | % Selectivity* to IBAC (molar basis) |
|---|---|---|---|---|---|---|---|
| Example 8 | 0.58 | 5.4 | 0.54 | 1.54 | 1.02 | 0.44 | 93.6 |
| Example 9 | 0.58 | 5.4 | 2.02 | 1.83 | 1.20 | 0.61 | 93.1 |
| Example 10 | 0.62 | 5.5 | 3.66 | 2.28 | 1.15 | 0.74 | 92.0 |

*Based on the reacted IBD

When the results of Examples 8 and 9 are compared with those of Example 10, it is clear than when the water content of the reaction solution is higher than 2.5 percent by weight, the selectivity to IBAC is low.

EXAMPLE 11

A 34 l jacketed bubbling-column reactor was charged with 26 l of IBAC containing 0.1 mol/l of IBAK, and was heated to 60° C. with a gas containing 9.35% $O_2$ being fed at a rate of 12.63 Nm³/hr. Subsequently, a solution of IBAC/IBAK/$H_2O$ at a molar ratio of 5.87:0.53:2.28 and IBD were fed at rates of 0.62 l/hr.

and 5.32 l/hr., respectively (molar ratio of O₂ to IBD:0.88), and the reactor was operated at 60° C. and at a pressure of 6 kg/cm² (gage) with an average residence time of 4.3 hours. The oxygen concentration of the reactor off-gas was 4.5% by volume.

The gas-chromatographic analysis of the resulting reaction solution gave the data of selectivities to by-products and IBAC and conversion of IBD as indicated in the Table 3 below.

Thereafter the reaction solution was passed into a 300 ml jacketed reaction vessel equipped with a stirrer at a feed rate of 113 cc/hr., while air being also fed at a rate of 6.4 Nl/hr., and the reaction vessel was operated at 70° C. and at a pressure of 5 kg/cm² (gage) for 3 hours. The oxygen concentration of the reactor off-gas was 5.8% by volume.

The gas-chromatographic analysis of the resulting reaction solution gave the data as indicated in the Table 3 below in terms of selectivities to by-products and IBAC and conversion of IBD.

EXAMPLE 12

Only the first-stage oxidation was conducted with a residence time of 8 hours while a gas containing 5.8% O₂, IBD and the IBAC/IBAK/H₂O solution being fed at rates of 11.66 Nm³/hr., 2.55 l/hr. and 0.36 l/hr., respectively (molar ratio of O₂ to IBD:1.06). The oxygen concentration of the reactor off-gas was 4.2% by volume.

The gas-chromatographic analysis of the resulting reaction solution gave the data of selectivities to by-products and IBAC and conversion of IBD as indicated in the following Table 3.

TABLE 3

|  | | % Selectivity* to by-products (molar basis) | | | % Selectivity* to IBAC (molar basis) | % Conversion of IBD (molar basis) |
|---|---|---|---|---|---|---|
|  | | AT | PO | IPA | | |
| Example 11 | 1st Stage | 1.66 | 1.09 | 0.31 | 96.0 | 90 |
|  | 2nd Stage | 1.9 | 1.14 | 0.31 | 95.6 | 98.8 |
| Example 12 | | 3.22 | 1.06 | 0.33 | 93.9 | 92.6 |

*Based on the reacted IBD

EXAMPLE 13

A 34 l jacketed bubbling-column reactor was charged with 25 l of IBAC containing 0.1 mol/l of IBAK and was heated to 60° C. with a gas containing 11.7% oxygen being fed at a rate of 12.1 Nm³/hr. Subsequently, a solution consisting of 67.7% IBAC, 6.12% IBAK and 26.2% H₂O on a molar basis and IBD were fed at rates of 0.96 l/hr. and 8 l/hr., respectively (molar ratio of O₂ to IBD:0.71), and the reactor was operated at 60° C. and at a pressure of 6 kg/cm² (gage) with an average residence time of 3 hours.

The overflowing reaction solution was passed to a circulating tank and recycled to the bottom portion of the reactor at such a rate that the recycled solution has an internal linear velocity of 44.5 m/hr.

The reaction solution was sampled from the circulating tank and analyzed by means of gas-chromatography to determine the composition of the reaction solution. The off-gas stripped from the overhead was passed through a condenser and demisted before it was subjected to gas-chromatographic analysis to determine its composition. The oxygen concentration of the reactor off-gas was 4.2% by volume.

Table 4 shows the data thus obtained in terms of selectivities to by-products AT, PO and IPA, selectivities to the desired IBAC, conversion of IBD and rate constant.

EXAMPLE 14

Example 13 was repeated except that the circulation of the reaction solution was omitted. The oxygen concentration of the reactor off-gas was 5.2% by volume.

The data obtained in this example in terms of selectivities to AT, PO, IPA and IBAC, conversion of IBD and rate constant are also included in Table 4 below.

TABLE 4

|  | % Selectivity to by-products (molar basis) | | | % Selectivity* to IBAC (molar basis) | % Conversion of IBD (molar basis) | Rate constant (mol/l · hr) |
|---|---|---|---|---|---|---|
|  | AT | PO | IPA | | | |
| Example 13 | 2.65 | 1.18 | 0.40 | 94.3 | 84.8 | 3.00 |
| Example 14 | 2.94 | 1.36 | 0.26 | 94.0 | 74.6 | 2.40 |

*Based on the reacted IBD

What is claimed as new and intended to be covered by Letters Patent is:

1. In a process for preparing isobutyric acid by continuous liquid-phase oxidation of isobutyraldehyde with molecular oxygen or a molecular oxygen-containing gas in the presence of an alkali metal-containing compound, the improvement comprising maintaining the molar ratio of oxygen to isobutyraldehyde to be fed at 0.5 or above wherein the oxygen concentration of the reactor off-gas is between 1 percent by volume and the lower explosion limit, the water content of the reaction solution is maintained at 2.5 percent by weight or below and the amount of alkali metal containing compound is 0.01 to 1 mole per liter of reaction solution.

2. The process according to claim 1 wherein the oxidation is conducted in a first stage in a bubbling column at a temperature of 50° to 70° C. with the percent conversion being kept at 95% or below and subsequently the effluent of the bubbling column is subjected to further oxidation in a second stage in at least one stirred tank reactor at a temperature equal to or higher than the temperature employed in the first-stage oxidation.

* * * * *